United States Patent [19]

Lafon

[11] 4,409,242
[45] Oct. 11, 1983

[54] 4-PHENOXY-3-HYDROXY-BUTYRAMIDOXIME DERIVATIVES

[75] Inventor: Louis Lafon, Paris, France

[73] Assignee: Laboratoire L. Lafon, Maisons-Alfort, France

[21] Appl. No.: 360,057

[22] Filed: Mar. 19, 1982

[30] Foreign Application Priority Data

Mar. 31, 1981 [FR] France ................................ 81 06469

[51] Int. Cl.³ .................. A61K 31/155; C07C 131/00
[52] U.S. Cl. ..................................... 424/326; 564/229
[58] Field of Search ........................ 564/229; 424/326

[56] References Cited

FOREIGN PATENT DOCUMENTS 2210388 7/1974 France .

*Primary Examiner*—Natalie Trousof
*Assistant Examiner*—L. Hendriksen

*Attorney, Agent, or Firm*—Poms, Smith, Lande & Rose

[57] ABSTRACT

The present invention relates as new industrial products to 4-phenoxy-3-butyramidoxime derivatives, characterized in that they are selected from the group consisting of 4-(allylphenoxy)-3-hydroxy-butyramidoximes of formula:

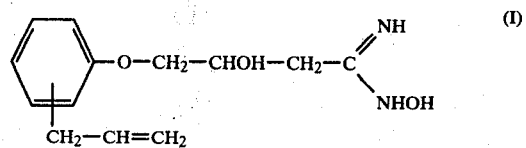

and addition salts thereof. These products are useful in therapeutics, particularly as antiarrythmic agents. The compounds of formula I are prepared by reacting the corresponding butyronitrile with hydroxylamine.

3 Claims, No Drawings

4-PHENOXY-3-HYDROXY-BUTYRAMIDOXIME DERIVATIVES

The present invention relates to new 4-phenoxy-3-butyramidoxime derivatives as industrial products. It also relates to a method for preparing same and to their use in therapeutics, particularly as substances acting on the cardiovascular system.

4-phenoxy-3-hydroxy-butyramidoxime derivatives have already been described. French Pat. No. 71 29685 in particular discloses the hydrochloride of 4-(3,5-dimethoxyphenoxy)-3-hydroxy-butyramidoxime, and French Pat. No. 72 44573 discloses the hydrochloride of 4-(3,5-dimethylphenoxy)-3-hydroxy-butyramidoxime. Furthermore, French Pat. No. 70 24016 describes the hydrochloride of 4-(α-naphthyloxy)-3-hydroxy-butyramidoxime. These known products act on the cardiovascular system as anti-arrythmic agents. Among them, the hydrochloride of 4-(α-naphthyloxy)-3-hydroxy-butyramidoxime (having Code No. LL 1530) has been marketed as anti-arrythmic drug under the trademark Bradyl (International Common Name: Nadoxolol).

It has been unexpectedly found that new derivatives belonging to the family of the 4-phenoxy-3-hydroxy-butyramidoxime, which are structurally different from the knonw products (due to the presence of an allyl group on the phenyl ring) present advantageous cardiovascular properties from the therapeutical standpoint, particularly in the treatment of disorders of the cardiac rhythm.

A new derivative according to the invention belonging to the 4-phenoxy-3-hydroxy-butyramidoxime family is characterised in that it is selected from the group consisting of (i) 4-(allylphenoxy)-3-hydroxy-butyramidoximes of general formula:

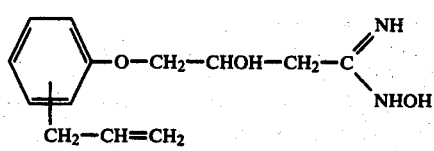

and (ii) addition salts thereof.

Addition salts are understood here to mean the acid addition salts (obtained by reacting a free base of formula I with a mineral or organic acid), and the ammonium salts. From acids which may be used for salifying the bases of formula I, particular mention may be made of hydrochloric, hydrobromic, nitric, sulfuric, acetic, propionic, oxalic, fumaric, maleic, succinic, benzoic, cinnamic, mandelic, citric, malic, tartric, p-toluenesulfonic and methanesulfonic acids. From the compounds enabling ammonium salts to be obtained, particular mention may be made of $ICH_3$ and $ClCH_3$. The acid addition salts are generally preferred to the ammonium salts.

The invention therefore relates to 4-(2-allylphenoxy)-, 4-(3-allylphenoxy)- and 4-(4-allylphenoxy)-3-hydroxy-butyramidoximes and their addition salts. The preferred products from the therapeutical standpoint are 4-(2-allylphenoxy)-3-hydroxy-butyramidoxime and addition salts thereof (particularly the hydrochloride) which are particularly advantageous as antiarrythmic agents.

The compounds of formula I may be prepared according to a known method by application of conventional reaction mechanisms. The method recommended according to the invention for preparing a compound of formula I is characterised in that a 4-(allylphenoxy)-3-hydroxy-butyronitrile of formula:

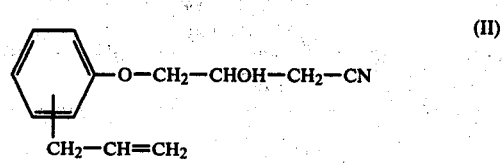

is reacted with hydroxylamine, in a $C_1$–$C_4$ alkanol-water reaction medium, for at least one hour, at the temperature of reflux of said reaction medium, with an excess of hydroxylamine with respect to the stoichiometric conditions.

In practice, more than one mol (about 2 mols will advantageously be taken) of $NH_2OH$ will be used for one mol of nitrile II, on the one hand, and a water-alcohol medium (0.5:1) to (1:0.5) v/v, on the other hand, the preferred alcohol being n-butanol.

The optical isomers of a compound of formula I may be isolated according to a method known per se for the resolution of the enantiomers particularly from the racemics.

According to the invention, a therapeutical composition is finally proposed, useful in particular in the treatment of disorders in the cardiac rythm and which is characterised in that it contains, in association with a physiologically acceptable excipient, at least one compound of formula I or one of its non-toxic salts. Such a composition will of course contain a pharmaceutically effective amount of active ingredient.

The following example of preparation is non-limiting but illustrates the best mode of procedure for synthesis.

PREPARATION

Obtaining of the hydrochloride of 4-(2-allylphenoxy)-3-hydroxybutyramidoxime:

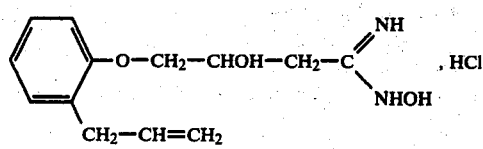

(Code No.: CRL 40708)

(a) 1-(o-allylphenoxy)-3-chloro-2-propanol

In a flask are placed 92.5 g (1 mol) of epichlorohydrin, 33.5 g (0.25 mol) of o-allylphenol and 0.3 ml of pyridine is added. The mixture is taken to 80° C. in about 1 hour then the temperature is raised to 90° C. and maintained for about 6 hours until the phenol has disappeared completely. The mixture is then cooled and the excess of epichlorohydrin evaporated. The remaining oil is taken up in 100 ml chloroform and 50 ml of HCl ($d_4^{15}$ – 1.19) are slowly added. The organic phase is then washed two to three times in water then dried over $Na_2SO_4$. After evaporation of the chloroform, 56.6 g (yield: about 100%) are obtained of 1-(o-allylphenoxy)-3-chloro-2-propanol in the form of an oil, dark brown in colour.

(b) 4-(o-allylphenoxy)-3-hydroxy-butyronitrile

The oil previously obtained (≃0.25 mole) is dissolved in 150 ml of methanol and a solution of 22.75 g (0.35 mol) of potassium cyanide in 35 ml of water is added under reflux, dropwise. Once the addition is terminated, reflux is continued for about 1 hour then the mixture is cooled, filtered, the methanol is evaporated, the oil obtained taken up in toluene, washed several times with water up to neutral pH, dried and evaporated in vacuo. 48.9 g-yield 90%-of 4-(o-allylphenoxy)-3-hydroxybutyronitrile are obtained.

(c) 4-(o-allylphenoxy)-3-hydroxy-butyramidoxime

An aqueous solution of hydroxylamine is prepared from 39.06 g (0.562 mol) of hydroxylamine hydrochloride in 150 ml of water and from 56.2 g (0.562 mol) of potassium bicarbonate. 48.9 g (0.225 mol) of 4-(o-allylphenoxy)-3-hydroxy-butyronitrile previously dissolved in 250 ml of n-butanol are then added. The resulting mixture is taken to 80° C. in about 2 hours, then taken to reflux (94° C.) which is maintained for 5 hours. The mixture is cooled, the H$_2$O—CH$_3$(CH$_2$)$_2$CH$_2$OH mixture is evaporated, the residue of evaporation is taken up with ether, washed several times in water, dried and the ether is evaporated under reduced pressure. 48.5 g (yield 86%) of 4-(o-allyl-phenoxy)-3-hydroxybutyramidoxime are obtained in the form of a brown oil.

(d) CRL 40708

The hydrochloride is precipitated by addition of hydrochloric ethanol to a solution of the free base (obtained as indicated hereinabove) in ethyl acetate. To facilitate precipitation, a little ether will advantageously be added. After recrystallization in ethyl acetate, CRL 40708 is obtained (with a yield of 70%). inst. m.p.=94° C.

By proceeding as indicated hereinabove, the m and p isomers of the CRL 40708 are obtained from the m- and p-allylphenols.

The tests undertaken with the CRL 40708 according to the following protocol have been summarized: Guinea pigs (6 animals per dose) anaesthetized with urethane receive by I.V. injection the CRL 40708 (the control animals receive an I.V. injection of physiological serum), five minutes after, they receive by I.V. perfusion either aconitine nitrate or K-strophantine.

It is observed that, at the doses of 5 mg/kg, 10 mg/kg and 20 mg/kg, I.V., the CRL 40708 delays the appearance of all accidents of the electrocardiogram provoked by the aconitine nitrate and the K-strophantine, and, particularly at the dose of 20 mg/kg, I.V., is bradycardia-inducing.

After administration of the CRL 40708 by the oral route and by the intraduodenal route, the anti-arrythmic properties observed after intravenous administration are found. In fact, it is observed that (i) the CRL 40708 at doses of 25 mg/kg P.O. and 50 mg/kg I.D. significantly delays the appearance of all the accidents of the electrocardiogram provoked in the anaesthetized Guinea pig by aconitine nitrate and K-strophantine, and (ii) at the dose of 25 mg/kg I.D., it significantly delays the appearance of ventricular fibrillation.

It is also observed that, by I.D. route, the CRL 40708 differs from the LL 1530 mentioned above which is an anti-arrythmic agent of reference. By the I.D. route, the minimum anti-arrythmic dose of the CRL 40708 is close to 25 mg/kg whilst the LL 1530 is still inactive at 25 mg/kg.

In clinic, good results have been obtained in the treatment of disorders in the cardiac rythm in humans by administration of CRL 40708 as anti-arrythmic agent in the form of tablets or capsules (each containing 75 to 150 mg of CRL 40708) at a rate of 3 to 6 tablets or capsules per day, for at least one week.

What is claimed is:

1. A new 4-phenoxy-3-hydroxybutyramidoxime derivative selected from the group consisting of:
(i) 4-(allylphenoxy)-3-hydroxy-butyramidoximes of the general formula:

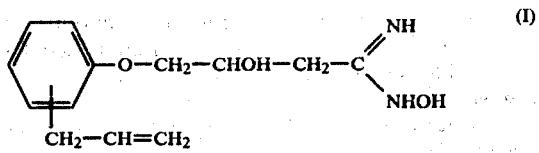

and,
(ii) addition salts thereof.

2. 4-(2-allylphenoxy)-3-hydroxybutyramidoxime and its addition salts.

3. A therapeutical composition comprising, in association with a physiologically acceptable excipient, a pharmaceutically effective amount of a compound according to claim 1 as antiarrythmic agent.

* * * * *